US012648748B2

(12) United States Patent　　(10) Patent No.: US 12,648,748 B2

Kawamura　　(45) Date of Patent: Jun. 9, 2026

(54) RADIATION IMAGE PROCESSING DEVICE, RADIATION IMAGE PROCESSING METHOD, AND RADIATION IMAGE PROCESSING PROGRAM

(71) Applicant: FUJIFILM Corporation, Tokyo (JP)

(72) Inventor: Takahiro Kawamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 367 days.

(21) Appl. No.: 18/333,379

(22) Filed: Jun. 12, 2023

(65) Prior Publication Data

US 2024/0023919 A1　　Jan. 25, 2024

(30) Foreign Application Priority Data

Jul. 19, 2022　(JP) ................................. 2022-115111

(51) Int. Cl.
*A61B 6/00*　　　(2024.01)

(52) U.S. Cl.
CPC .......... *A61B 6/5205* (2013.01); *A61B 6/5282* (2013.01)

(58) Field of Classification Search
None
See application file for complete search history.

(56) References Cited

U.S. PATENT DOCUMENTS

| | | | | | |
|---|---|---|---|---|---|
| 5,181,234 | A | * | 1/1993 | Smith | G01V 5/222 |
| | | | | | 378/146 |
| 7,110,493 | B1 | * | 9/2006 | Kotowski | G01V 5/222 |
| | | | | | 378/57 |
| 7,402,730 | B1 | * | 7/2008 | Sparks | A01K 67/0276 |
| | | | | | 435/325 |
| 2008/0269118 | A1 | * | 10/2008 | Aparicio | A61P 3/04 |
| | | | | | 800/9 |

(Continued)

FOREIGN PATENT DOCUMENTS

| | | |
|---|---|---|
| JP | 2015-043959 A | 3/2015 |
| JP | 2018-134205 A | 8/2018 |

(Continued)

OTHER PUBLICATIONS

An Office Action, "Notice of Reasons for Refusal," mailed by the Japanese Patent Office on Mar. 3, 2026, which corresponds to Japanese Patent Application No. 2022-115111, and is related to U.S. Appl. No. 18/333,379; with English language translation.

*Primary Examiner* — Helen Zong

(74) *Attorney, Agent, or Firm* — Studebaker Brackett PLLC

(57)　　　　ABSTRACT

A processor acquires a first radiation image and a second radiation image, which are acquired by imaging a subject with radiation having different energy distributions, derives a body thickness of the subject based on at least one of the first radiation image or the second radiation image, specifies a soft region of the subject in the first radiation image and the second radiation image, derives a first attenuation coef- (Continued)

RADIATION IMAGE PROCESSING DEVICE ficient and a second attenuation coefficient, which correspond to the body thickness in the soft region, for each of the first radiation image and the second radiation image, and derives an attenuation ratio, which is a ratio according to the body thickness between the first attenuation coefficient and the second attenuation coefficient, as an indicator representing a quality of the radiation.

7 Claims, 6 Drawing Sheets

(56) References Cited

U.S. PATENT DOCUMENTS

| | | | |
|---|---|---|---|
| 2016/0140720 A1 | 5/2016 | Naito | |
| 2018/0122094 A1 | 5/2018 | Naito | |
| 2018/0240224 A1 | 8/2018 | Fukuda | |
| 2018/0263559 A1* | 9/2018 | Kawamura | ............ A61B 6/032 |
| 2021/0106298 A1* | 4/2021 | Kawamura | .............. A61B 6/50 |
| 2022/0172365 A1 | 6/2022 | Kawamura | |
| 2022/0175333 A1 | 6/2022 | Kawamura | |

FOREIGN PATENT DOCUMENTS

| | | |
|---|---|---|
| JP | 2018-153605 A | 10/2018 |
| JP | 2021-058508 A | 4/2021 |
| JP | 2022-103615 A | 7/2022 |
| WO | 2021/054090 A1 | 3/2021 |
| WO | 2021/054091 A1 | 3/2021 |

* cited by examiner

RADIATION IMAGE PROCESSING DEVICE, RADIATION IMAGE PROCESSING METHOD, AND RADIATION IMAGE PROCESSING PROGRAM

CROSS REFERENCE TO RELATED APPLICATIONS

The present application claims priority from Japanese Patent Application No. 2022-115111, filed on Jul. 19, 2022, the entire disclosure of which is incorporated herein by reference.

BACKGROUND

Technical Field

The present disclosure relates to a radiation image processing device, a radiation image processing method, and a radiation image processing program.

Related Art

In the related art, energy subtraction processing using two radiation images obtained by irradiating a subject with two types of radiation having different energy distributions by using the fact that an attenuation amount of the transmitted radiation differs depending on the substance constituting the subject has been known. The energy subtraction processing is a method in which respective pixels of the two radiation images obtained as described above are associated with each other, and the pixels are multiplied by an appropriate weight coefficient and then subtracted to acquire an image in which specific compositions, such as a bone part and a soft part, included in the radiation image are separated.

In addition, various methods for deriving a composition of a human body, such as a bone mineral density, a fat, and a muscle, by the energy subtraction processing have also been proposed. For example, JP2018-153605A proposes a method in which a soft part image in which a soft part of a subject is extracted is generated from a plurality of radiation images acquired by radiation having different energy distributions transmitted through the subject, a body thickness distribution of the subject is estimated based on an imaging condition in a case in which the soft part image and the radiation image are acquired, an approximate body thickness distribution that approximates the estimated body thickness distribution with a model corresponding to a human body is calculated, and a distribution of the body fat percentage in the subject is calculated based on the approximate body thickness distribution.

SUMMARY OF THE INVENTION

As described above, the energy subtraction processing uses the radiation images acquired by the radiation having different energy distributions. Here, a quality of the radiation is changed due to an influence of a radiation source, a top plate, a scattered ray removal grid, and a radiation detector constituting an imaging apparatus. In particular, the radiation source has a temporal change in the quality of the radiation. In such a change in the quality of the radiation, the energy distributions of the radiation are different, and as a result, the separation accuracy of the composition by the energy subtraction processing is decreased. Here, the change in the quality of the radiation can be calibrated by measuring an aluminum semi-value layer. However, since the aluminum semi-value layer is a simple indicator of the quality of the radiation using aluminum as a material, the aluminum semi-value layer cannot be uniquely associated with the energy distribution of the radiation. For this reason, in the measurement of the quality of the radiation using the aluminum semi-value layer, the separation accuracy of the composition of the energy subtraction processing may not be sufficient. In addition, the work of measuring the aluminum semi-value layer imposes a heavy burden on the user.

SUMMARY OF THE INVENTION

The present disclosure has been made in view of the above circumstances, and is to make it possible to know a change in a quality of the radiation without imposing a burden on a user.

The present disclosure relates to a radiation image processing device comprising at least one processor, in which the processor acquires a first radiation image and a second radiation image, which are acquired by imaging a subject with radiation having different energy distributions, derives a body thickness of the subject based on at least one of the first radiation image or the second radiation image, specifies a soft region of the subject in the first radiation image and the second radiation image, derives a first attenuation coefficient and a second attenuation coefficient, which correspond to the body thickness in the soft region, for each of the first radiation image and the second radiation image, and derives an attenuation ratio, which is a ratio according to the body thickness between the first attenuation coefficient and the second attenuation coefficient, as an indicator representing a quality of the radiation.

Note that, in the radiation image processing device according to the present disclosure, the processor may derive a first primary ray image and a second primary ray image by removing scattered ray components of the first radiation image and the second radiation image, and derive the first attenuation coefficient and the second attenuation coefficient based on the first primary ray image and the second primary ray image.

In addition, in the radiation image processing device according to the present disclosure, the indicator may represent a relationship between the body thickness and the attenuation ratio.

In addition, in the radiation image processing device according to the present disclosure, the processor may determine whether or not a difference between the indicator and a standard indicator exceeds a predetermined threshold value, and issue a warning in a case in which a negative determination is made in the determination.

The present disclosure relates to a radiation image processing method comprising acquiring a first radiation image and a second radiation image, which are acquired by imaging a subject with radiation having different energy distributions, deriving a body thickness of the subject based on at least one of the first radiation image or the second radiation image, specifying a soft region of the subject in the first radiation image and the second radiation image, deriving a first attenuation coefficient and a second attenuation coefficient, which correspond to the body thickness in the soft region, for each of the first radiation image and the second radiation image, and deriving an attenuation ratio, which is a ratio according to the body thickness between the first attenuation coefficient and the second attenuation coefficient, as an indicator representing a quality of the radiation.

The present disclosure relates to a radiation image processing program causing a computer to execute a procedure of acquiring a first radiation image and a second radiation image, which are acquired by imaging a subject with radiation having different energy distributions, a procedure of deriving a body thickness of the subject based on at least one of the first radiation image or the second radiation image, a procedure of specifying a soft region of the subject in the first radiation image and the second radiation image, a procedure of deriving a first attenuation coefficient and a second attenuation coefficient, which correspond to the body thickness in the soft region, for each of the first radiation image and the second radiation image, a procedure of deriving an attenuation ratio, which is a ratio according to the body thickness between the first attenuation coefficient and the second attenuation coefficient, as an indicator representing a quality of the radiation.

According to the present disclosure, it is possible to know the change in the radiation quality without imposing the burden on the user.

DETAILED DESCRIPTION

Figure 1:
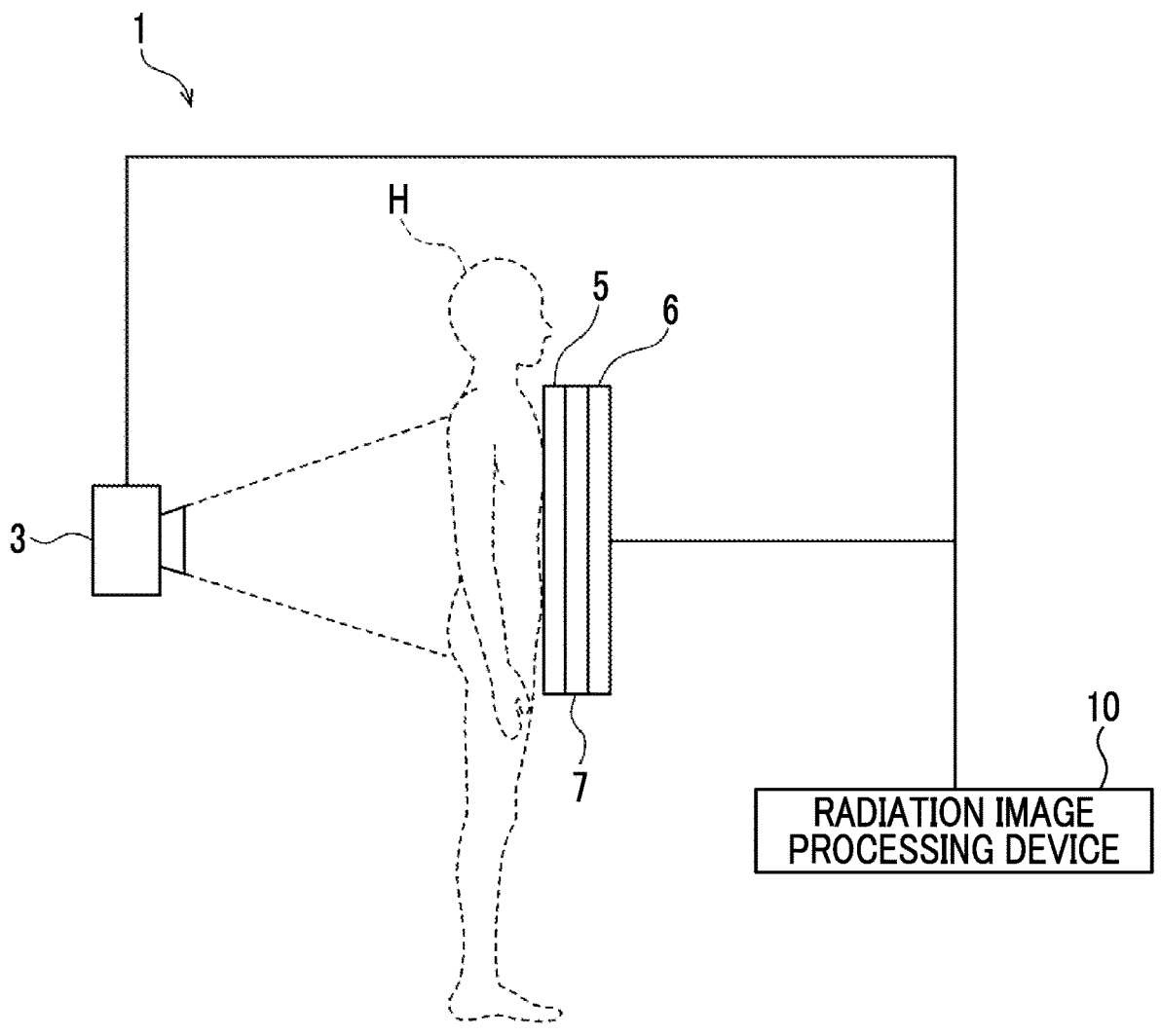
FIG. 1 is a schematic block diagram showing a configuration of a radiography system to which a radiation image processing device according to an embodiment of the present disclosure is applied.

In the following description, an embodiment of the present disclosure will be described with reference to the drawings. FIG. 1 is a schematic block diagram showing a configuration of a radiography system to which a radiation image processing device according to the present embodiment of the present disclosure is applied. As shown in FIG. 1, the radiography system according to the present embodiment comprises an imaging apparatus 1 and a radiation image processing device 10 according to the present embodiment.

The imaging apparatus 1 is an imaging apparatus for performing energy subtraction by a so-called one-shot method for converting radiation, such as X-rays, emitted from a radiation source 3 and transmitted through a subject H into energy and irradiating a first radiation detector 5 and a second radiation detector 6 with the converted radiation. During the imaging, as shown in FIG. 1, the first radiation detector 5, a radiation energy conversion filter 7 made of a copper plate or the like, and the second radiation detector 6 are disposed in order from a side closest to the radiation source 3, and the radiation source 3 is driven. Note that the first and second radiation detectors 5 and 6 are closely attached to the radiation energy conversion filter 7.

As a result, in the first radiation detector 5, a first radiation image G1 of the subject H by low-energy radiation also including so-called soft rays is acquired. In addition, in the second radiation detector 6, a second radiation image G2 of the subject H by high-energy radiation from which the soft rays are removed is acquired. The first and second radiation images G1 and G2 are input to the radiation image processing device 10.

Note that, in the present embodiment, a scattered ray removal grid that removes a scattered ray component of the radiation transmitted through the subject H is not used during the imaging of the subject H. Therefore, the first radiation image G1 and the second radiation image G2 also include a primary ray component and the scattered ray component of the radiation transmitted through the subject H.

Here, the energy subtraction processing is processing of generating an image in which different tissues (for example, a soft part and a bone part) in the subject are extracted by using two radiation images obtained by irradiating the subject with two types of radiation having different energy distributions by using the fact that an attenuation amount of the transmitted radiation differs depending on the substance constituting the subject.

The first and second radiation detectors 5 and 6 can perform recording and reading-out of the radiation image repeatedly. A so-called direct-type radiation detector that directly receives emission of the radiation and generates an electric charge may be used, or a so-called indirect-type radiation detector that converts the radiation into visible light and then converts the visible light into an electric charge signal may be used. In addition, as a method for reading out a radiation image signal, it is desirable to use a so-called thin film transistor (TFT) readout method in which the radiation image signal is read out by turning a TFT switch on and off, or a so-called optical readout method in which the radiation image signal is read out by emission of read out light. However, other methods may also be used without being limited to these methods.

Figure 2:
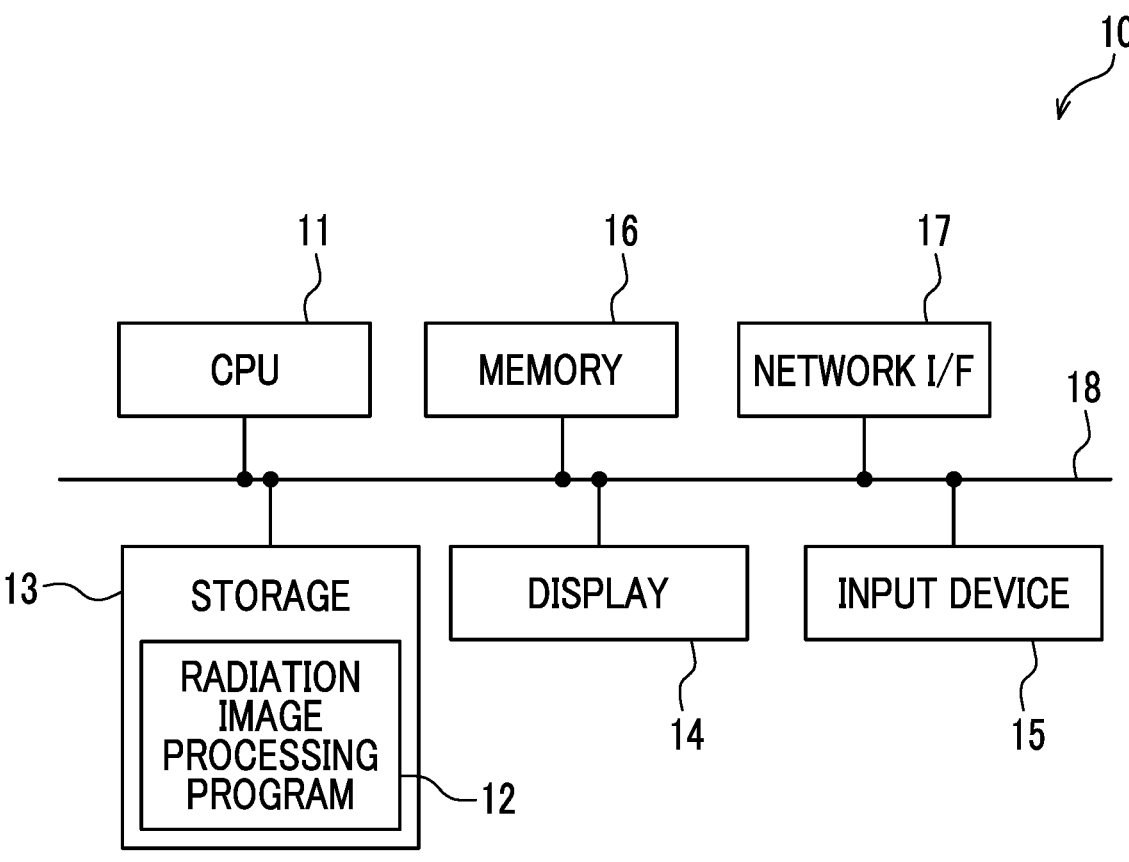
FIG. 2 is a diagram showing a schematic configuration of the radiation image processing device according to the present embodiment.

Then, the radiation image processing device according to the present embodiment will be described. First, with reference to FIG. 2, a hardware configuration of the radiation image processing device according to the present embodiment will be described. As shown in FIG. 2, the radiation image processing device 10 is a computer, such as a workstation, a server computer, and a personal computer, and comprises a central processing unit (CPU) 11, a non-volatile storage 13, and a memory 16 as a transitory storage region. In addition, the radiation image processing device 10 comprises a display 14, such as a liquid crystal display, an input device 15, such as a keyboard and a mouse, and a network interface (UF) 17 connected to a network (not shown). The CPU 11, the storage 13, the display 14, the input device 15, the memory 16, and the network OF 17 are connected to a bus 18. Note that the CPU 11 is an example of a processor according to the present disclosure.

The storage 13 is realized by a hard disk drive (HDD), a solid state drive (SSD), a flash memory, and the like. A radiation image processing program 12 installed in the radiation image processing device 10 is stored in the storage 13 as a storage medium. The CPU 11 reads out the radiation image processing program 12 from the storage 13, expands the read out radiation image processing program 12 to the memory 16, and executes the expanded radiation image processing program 12.

The radiation image processing program 12 is stored in a storage device of the server computer connected to the network or in a network storage in a state of being accessible from the outside, and is downloaded and installed in the computer that configures the radiation image processing device 10 in response to the request. Alternatively, the radiation image processing program 12 is distributed in a state of being recorded on a recording medium, such as a digital versatile disc (DVD) or a compact disc read only memory (CD-ROM), and is installed in the computer that configures the radiation image processing device 10 from the recording medium.

Figure 3:
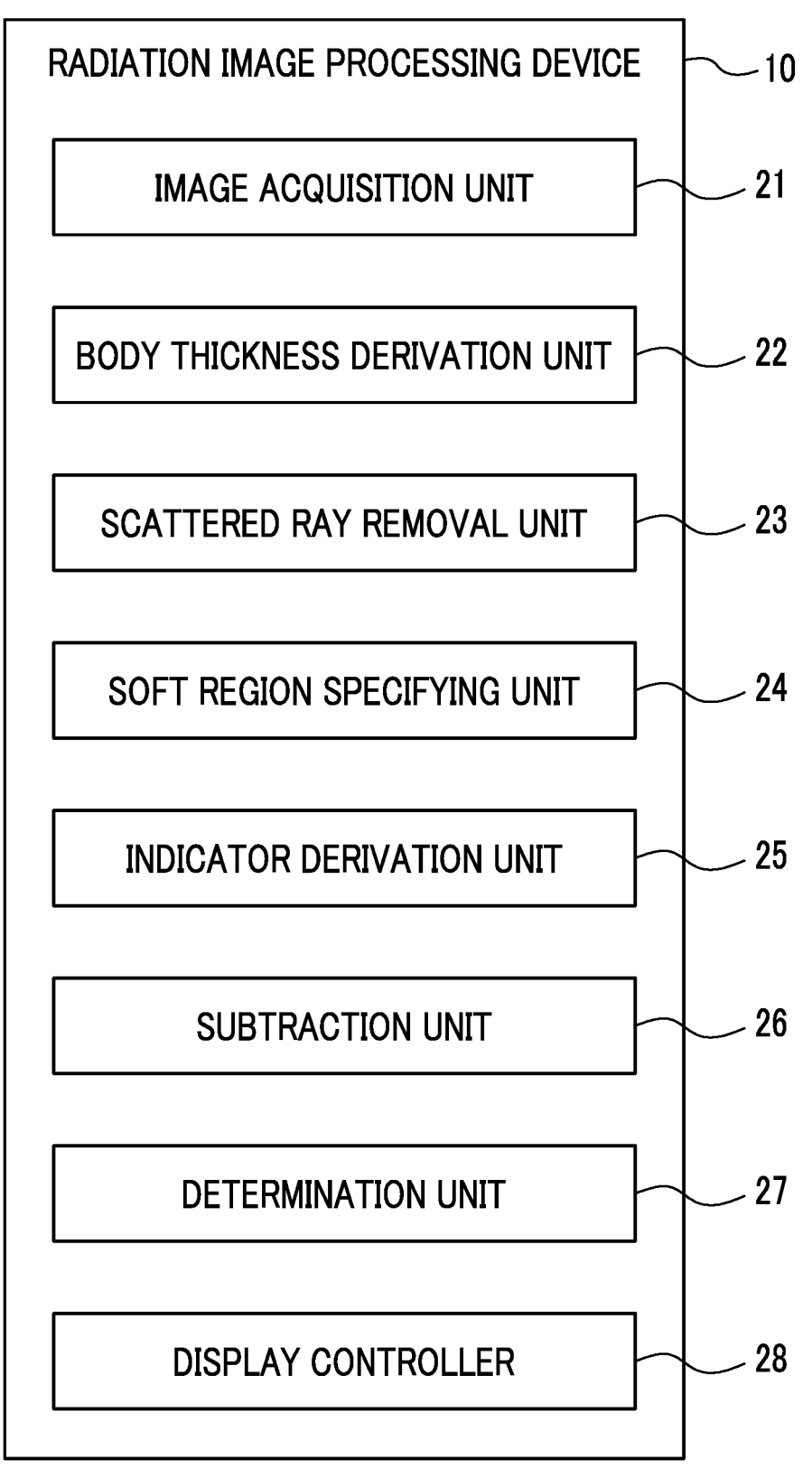
FIG. 3 is a diagram showing a functional configuration of the radiation image processing device according to the present embodiment.

Then, a functional configuration of the radiation image processing device according to the present embodiment will be described. FIG. 3 is a diagram showing the functional configuration of the radiation image processing device according to the present embodiment. As shown in FIG. 3, the radiation image processing device 10 comprises an image acquisition unit 21, a body thickness derivation unit 22, a scattered ray removal unit 23, a soft region specifying unit 24, an indicator derivation unit 25, a subtraction unit 26, a determination unit 27, and a display controller 28. Then, by executing the radiation image processing program 12, the CPU 11 functions the image acquisition unit 21, the body thickness derivation unit 22, the scattered ray removal unit 23, the soft region specifying unit 24, the indicator derivation unit 25, the subtraction unit 26, the determination unit 27, and the display controller 28.

The image acquisition unit 21 acquires the first radiation image G1 and the second radiation image G2 of the subject H from the first and second radiation detectors 5 and 6 by causing the imaging apparatus 1 to perform the energy subtraction imaging of the subject H. In this case, imaging conditions, such as an imaging dose, an energy distribution, a tube voltage, and an SID, are set. The imaging conditions need only be set by input from the input device 15 by a user. The set imaging conditions are stored in the storage 13. Note that the first and second radiation images G1 and G2 may be acquired by a program different from the radiation image processing program according to the present embodiment. In this case, the image acquisition unit 21 reads out the first and second radiation images G1 and G2 stored in the storage 13 from the storage 13 for processing.

The body thickness derivation unit 22 derives the body thickness of the subject H for each pixel of the first and second radiation images G1 and G2 based on at least one image of the first radiation image G1 or the second radiation image G2. Since the body thickness is derived for each pixel of the first and second radiation images G1 and G2, the body thickness derivation unit 22 derives the body thickness distribution in at least one of the first radiation image G1 or the second radiation image G2. In a case of deriving the body thickness, the body thickness derivation unit 22 uses the first radiation image G1 acquired by the radiation detector 5 on the side close to the subject H. However, the second radiation image G2 may be used. In addition, regardless of which image is used, a low-frequency image representing a low-frequency component of the image may be derived, and the body thickness may be derived by using the low-frequency image.

In the present embodiment, the body thickness derivation unit 22 derives the body thickness of the subject H by assuming that a brightness distribution of the first radiation image G1 coincides with the body thickness distribution of the subject H, and converting the pixel value of the first radiation image G1 into the thickness by using an attenuation coefficient of the soft part of the subject H. Instead of the above, the body thickness derivation unit 22 may measure the thickness of the subject H by using a sensor or the like. Also, the body thickness derivation unit 22 may derive the body thickness by approximating the body thickness of the subject H with a model such as a cube or an elliptical column. In addition, the body thickness derivation unit 22 may derive the body thickness of the subject H simultaneously with scattered ray removal processing by the scattered ray removal unit 23 described below.

The scattered ray removal unit 23 removes the scattered ray component generated by the scattering of the radiation in the subject, which is included in the first and second radiation images G1 and G2. As a method for removing the scattered ray component, for example, any method disclosed in JP2015-043959A, can be used. The method disclosed in JP2015-043959A is a method for performing the scattered ray removal processing of the radiation image by deriving the scattered ray component using the derived body thickness. Note that, in the following description, the first and second radiation images G1 and G2 from which the scattered ray components are removed will be referred to as a first primary ray image Gp1 and a second primary ray image Gp2.

Here, the scattered ray removal in a case in which the method disclosed in JP2015-043959A is used will be described. In a case in which a method disclosed in JP2015-043959A or the like is used, the derivation of the body thickness and the derivation of the scattered ray component for removing the scattered rays are performed simultaneously with each other.

Therefore, the derivation of the body thickness and the removal of the scattered rays are performed in the body thickness derivation unit 22 and the scattered ray removal unit 23 as follows. First, the body thickness derivation unit 22 and the scattered ray removal unit 23 acquire a virtual model of the subject H having an initial body thickness distribution, and derive an estimation primary ray image in which a primary ray image obtained by imaging of the virtual model is estimated, and an estimation scattered ray image in which a scattered ray image obtained by the imaging of the virtual model is estimated. Note that, in the present embodiment, the derivation of the estimation primary ray image and the estimation scattered ray image is performed by using the first radiation image G1. Next, the body thickness derivation unit 22 and the scattered ray removal unit 23 add the estimation primary ray image and the estimation scattered ray image to derive an estimation image. Further, the body thickness derivation unit 22 and the scattered ray removal unit 23 modify the initial body thickness distribution such that a difference between the estimation image and the first radiation image G1 is small.

Then, the body thickness derivation unit 22 and the scattered ray removal unit 23 derive the estimation image by using the modified body thickness distribution, and repeatedly perform the generation of the estimation image using the modified body thickness distribution and the modifying of the body thickness distribution until the difference between the estimation image and the first radiation image G1 satisfies a predetermined termination condition. The body thickness derivation unit 22 derives the body thickness distribution in a case in which the termination condition is satisfied as the body thickness of the subject H. The scattered ray removal unit 23 removes the scattered ray component from the first radiation image G1 by subtracting the estimation scattered ray image in a case in which the termination condition is satisfied from the first radiation image G1, and derives the first primary ray image Gp1. Note that the scattered ray removal unit 23 derives the estimation scattered ray image for the second radiation image G2 in the same manner as in the first radiation image G1, removes the scattered ray component from the second radiation image G2 by subtracting the derived estimation scattered ray image from the second radiation image G2, and derives the second primary ray image Gp2.

The soft region specifying unit 24 specifies a region of the soft tissue (hereinafter, referred to as a soft region) in the first and second primary ray images Gp1 and Gp2. Here, in the radiation image, the bone part appears as a region having relatively high brightness (low concentration) because the radiation transmittance is low, and the soft part appears as a region having relatively low brightness (high concentration) because the radiation transmittance is higher than the radiation transmittance in the bone part. Therefore, in the first and second primary ray images Gp1 and Gp2, the soft region specifying unit 24 specifies a region in which the brightness is equal to or less than a predetermined threshold value as the soft region.

Note that the soft region specifying unit 24 may specify the soft region in the first and second primary ray images Gp1 and Gp2 by using a trained model that has been subjected to machine learning to specify the soft region in the radiation image. In addition, the soft region specifying unit 24 may specify the soft region by displaying the first and second primary ray images Gp1 and Gp2 on the display 14 and receiving an instruction for specifying the soft region by the user.

The indicator derivation unit 25 derives a first attenuation coefficient $\mu1$ and a second attenuation coefficient $\mu2$ according to the body thickness in the soft region for each of the first radiation image G1 and the second radiation image G2. In addition, the indicator derivation unit 25 derives an attenuation ratio, which is a ratio between the first attenuation coefficient $\mu1$ and the second attenuation coefficient $\mu2$ according to the body thickness, as an indicator representing a quality of the radiation.

In the present embodiment, the indicator derivation unit 25 derives the first attenuation coefficient $\mu1$ and the second attenuation coefficient $\mu2$ based on the first primary ray image Gp1 and the second primary ray image Gp2. Here, the relationship between the attenuation coefficient and a primary dose during the imaging of the radiation image is represented by Expression (1). In Expression (1), Ip is a primary dose which is a dose transmitted through the subject H and reaching the radiation detector, I0 is a reaching dose of the radiation reaching the radiation detector without being transmitted through the subject H, and $\mu(t)$ is an attenuation coefficient of the radiation of the soft tissue of the subject H. The attenuation coefficient of the radiation depends on the body thickness t.

$$Ip=I0\times\exp(-\mu(t)\cdot t) \tag{1}$$

A relationship between the primary dose Ip1 and the first attenuation coefficient $\mu1$ with respect to the first primary ray image Gp1 and a relationship between the primary dose Ip2 and the second attenuation coefficient $\mu2$ with respect to the second primary ray image Gp2 are represented by Expression (2) and Expression (3). Note that, in Expression (2) and Expression (3), (x,y) representing the position of the pixel is omitted. Note that Id1 and Id2 are the reaching doses that reach the first radiation detector 5 and the second radiation detector 6 without being transmitted through the subject H.

$$Ip1=Id1\times\exp(-\mu(t)\cdot t) \tag{2}$$

$$Ip2=Id2\times\exp(-\mu2(t)\cdot t) \tag{3}$$

From Expression (2) and Expression (3), the first attenuation coefficient $\mu1$ and the second attenuation coefficient $\mu2$ are represented by Expression (4) and Expression (5).

$$\exp(-\mu1(t)\cdot t)=Ip1/Id1 \tag{4}$$

$$\exp(-\mu(t)\cdot t)=Ip2/Id2 \tag{5}$$

Therefore, the first attenuation coefficient $\mu1$ and the second attenuation coefficient $\mu2$ are represented by Expression (6) and Expression (7).

$$\mu1(t)\cdot t=-\log(Ip1/Id1)=\log Id1-\log Ip1 \tag{6}$$

$$\mu2(t)\cdot t=-\log(Ip2/Id2)=\log Id2-\log Ip2 \tag{7}$$

Here, log Ip1 is a pixel value of a soft region in the first primary ray image Gp1. log Id1 is a pixel value of a direct radiation region in the first primary ray image Gp1. log Ip2 is a pixel value of a soft region in the second primary ray image Gp2. log Id2 is a pixel value of a direct radiation region in the second primary ray image Gp2. Therefore, an attenuation ratio R0 between the first attenuation coefficient $\mu1$ and the second attenuation coefficient $\mu2$ is represented by Expression (8).

$$R0(t)=\{\mu1(t)\cdot t\}/\{\mu2(t)\cdot t\}=\mu1(t)/\mu2(t)=(Gd1-Gp1)/ \\ (Gd2-Gp2) \tag{8}$$

Figure 4:
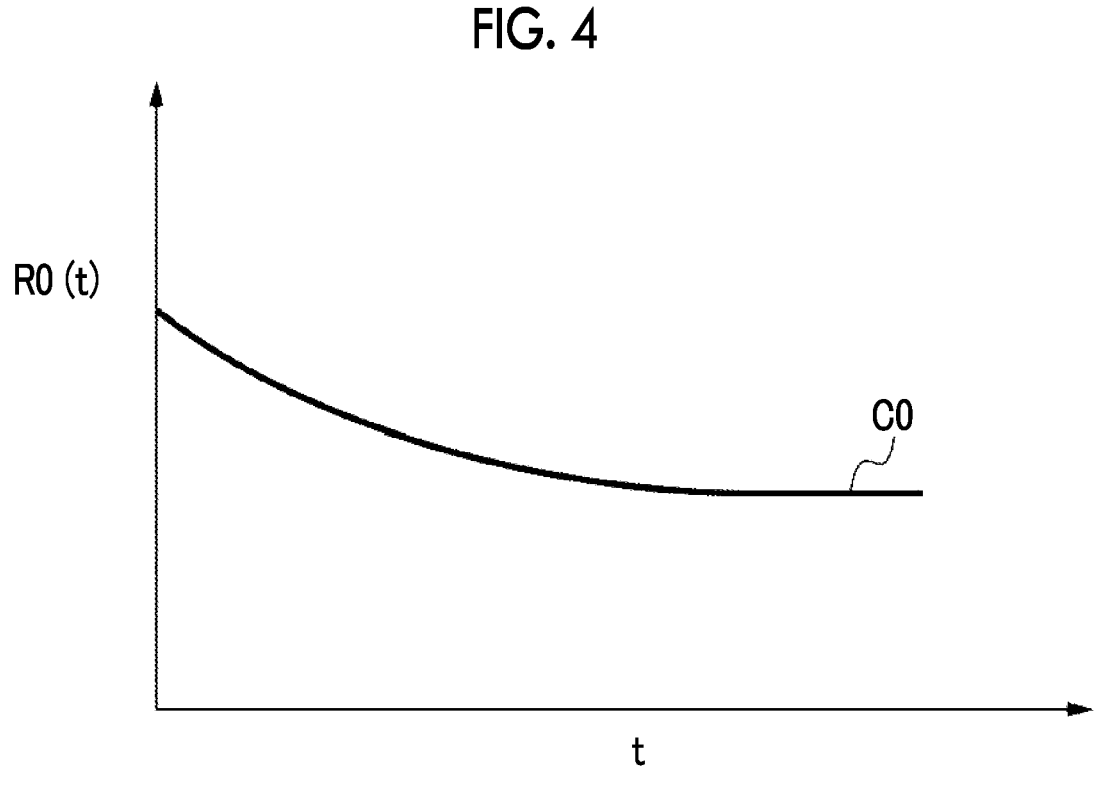
FIG. 4 is a diagram showing an attenuation ratio according to a body thickness.

The indicator derivation unit 25 derives the attenuation ratio R0(t) based on the first primary ray image Gp1 and the second primary ray image Gp2 according to Expression (8). Note that the attenuation ratio R0(t) is a ratio of the attenuation coefficient of the radiation having low energy to the attenuation coefficient of the radiation having high energy. FIG. 4 is a diagram showing the indicator, that is, the attenuation ratio according to the body thickness. As shown in FIG. 4, the attenuation ratio R0 is gradually decreased as the body thickness t is increased. Then, the indicator derivation unit 25 derives the attenuation ratio R0(t) according to the body thickness t as the indicator C0 representing the quality of the radiation.

Here, immediately after the imaging apparatus 1 is installed, there is no temporal change in the quality of the radiation emitted from the radiation source 3. Therefore, in the present embodiment, immediately after the imaging apparatus 1 is installed, the attenuation ratio R0(t) is derived by using the first and second radiation images G1 and G2 acquired by performing the first energy subtraction imaging, and stores the attenuation ratio R0(t) in the storage 13 and/or an external server as a standard indicator Cb.

The subtraction unit 26 derives a bone part image Gb in which only the bone part of the subject H included in the first radiation image G1 and the second radiation image G2 is extracted and a soft part image Gs in which only the soft part is extracted, by performing the weighting subtraction between the corresponding pixels, on the first primary ray image Gp1 and the second primary ray image Gp2, as shown in Expression (9) and Expression (10). Note that $\alpha1$ and $\alpha2$ in Expression (9) and Expression (10) is a weighting coefficient and is derived based on an attenuation coefficient according to the radiation energy of the soft part and the bone part of the subject H. In addition, x and y are the coordinates of each pixel of the bone part image Gb. Note that, in the following description, the bone part image Gb and the soft part image Gs will be referred to as composition images.

$$Gb(x,y)=Gp1(x,y)-\alpha1\times Gp2(x,y) \tag{9}$$

$$Gs(x,y)=Gp2(x,y)-\alpha2\times Gp1(x,y) \tag{10}$$

Here, in the present embodiment, for the purpose of image diagnosis of the subject H, the composition images, such as the bone part image and the soft part image of the subject H, are derived from the first and second radiation images G1 and G2, or the first and second primary ray images Gp1 and Gp2. Therefore, in the present embodiment, the indicator C0 is derived each time the energy subtraction imaging for the image diagnosis of the subject H is performed.

Figure 5:
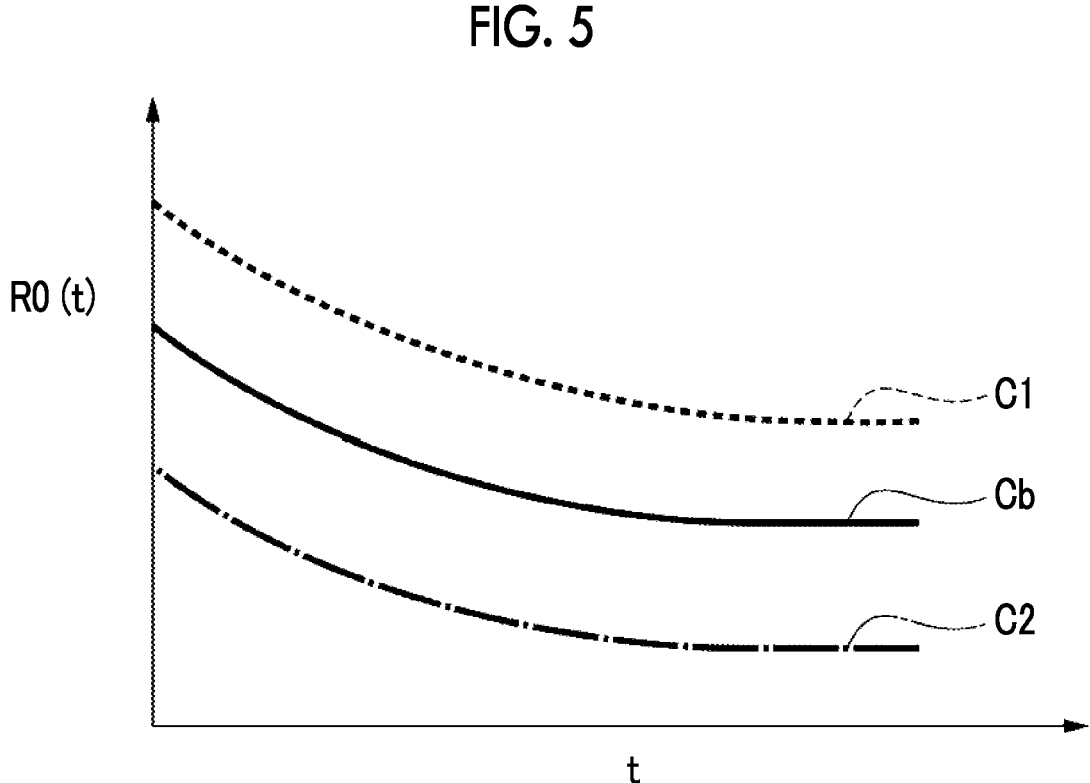
FIG. 5 is a diagram for describing a determination.

The determination unit 27 determines whether or not a difference between the derived indicator C0 and the standard indicator Cb exceeds a predetermined threshold value each time the energy subtraction imaging is performed. FIG. 5 is a diagram for describing the determination. The quality of the radiation emitted from the radiation source 3 is temporally changed. For example, in a case in which the quality of the radiation is softened, the radiation energy distribution is reduced, so that the attenuation ratio R0(t) is increased as shown in an indicator C1. On the contrary, in a case in which the quality of the radiation is hardened, the energy distribution of the radiation is increased, so that the attenuation ratio R0(t) is decreased as shown in an indicator C2.

In a case in which such the change in the quality of the radiation is large, the separation accuracy of the composition by the energy subtraction processing is decreased. Therefore, in the present embodiment, the determination unit 27 issues a warning in a case in which the difference between the indicator C0 derived by the indicator derivation unit 25 and the standard indicator Cb exceeds a predetermined threshold value Th1, and causes the user to perform the first calibration in order to compensate for the temporal change in the quality of the radiation. Here, as the difference, a representative value, such as the sum of the differences between the indicator C0 and the standard indicator Cb in all the body thicknesses, the average value, the median value, the minimum value, or the maximum value, can be used.

Figure 6:
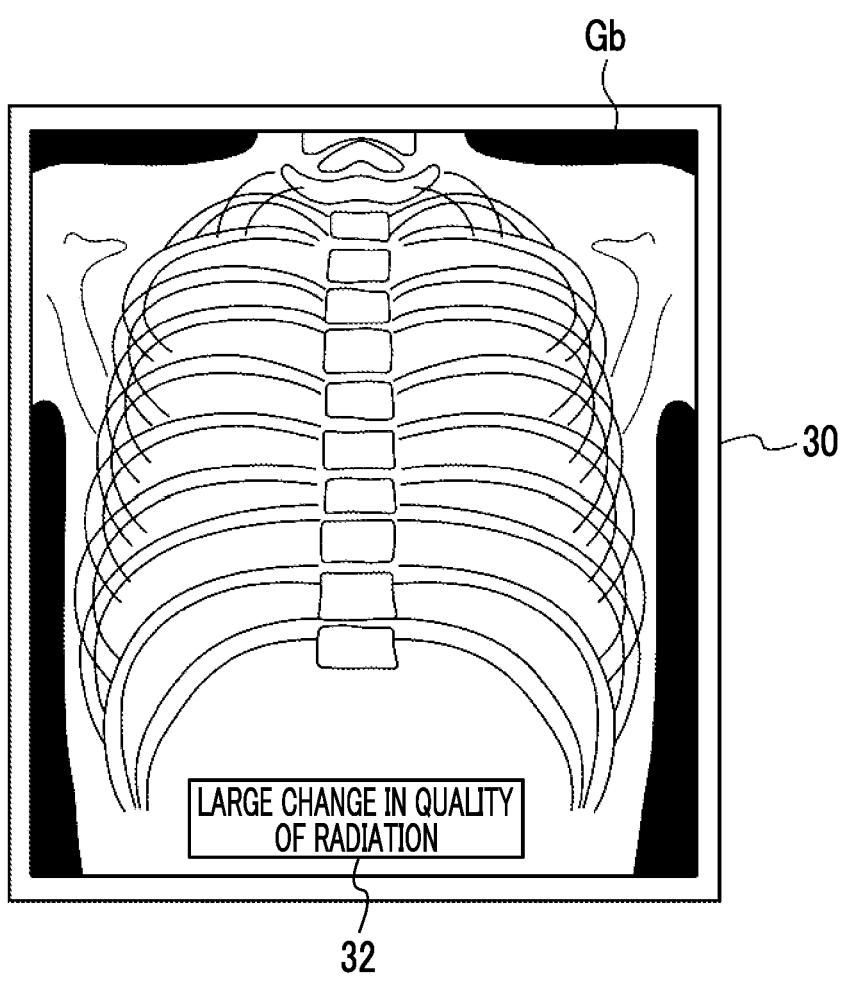
FIG. 6 is a diagram showing a display screen of a warning.

Note that the warning may be issued in a displayed manner on the display 14 or in an audible manner. FIG. 6 is a diagram showing an example of the displayed warning. As shown in FIG. 6, the bone part image Gb, which is the composition image derived by the energy subtraction processing, is displayed on the display screen 30. In addition, the text of "Large change in quality of radiation" is displayed as a warning 32.

Figure 7:
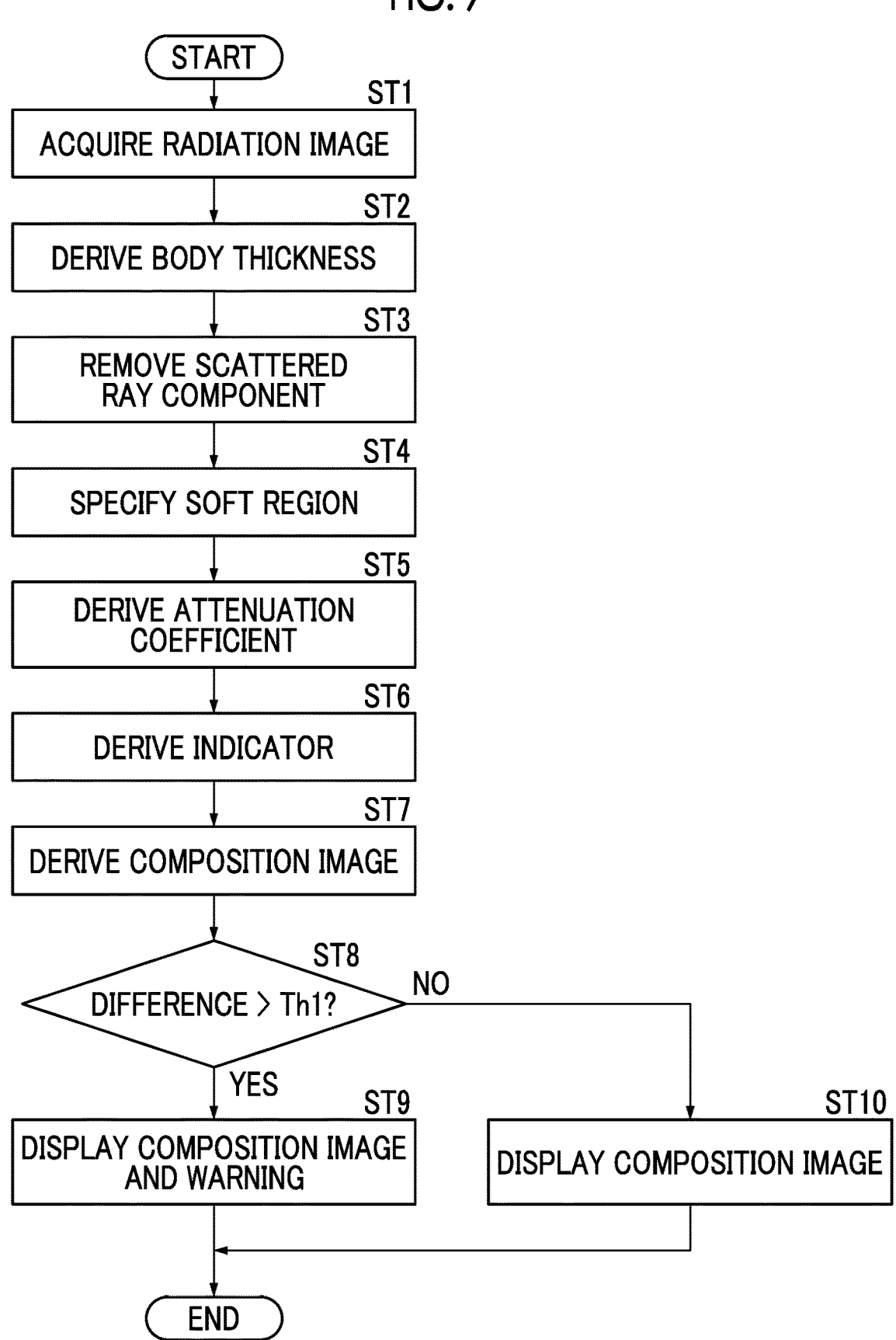
FIG. 7 is a flowchart showing processing performed in the present embodiment.

Then, processing performed in the present embodiment will be described. FIG. 7 is a flowchart showing the processing performed in the present embodiment. The image acquisition unit 21 causes the imaging apparatus 1 to perform the energy subtraction imaging of the subject H to acquire the first and second radiation images G1 and G2 (radiation image acquisition; step ST1). Next, the body thickness derivation unit 22 derives the body thickness of the subject H (step ST2), and the scattered ray removal unit 23 removes the scattered ray components from the first and second radiation images G1 and G2 to derive the first primary ray image Gp1 and the second primary ray image Gp2 (scattered ray removal: step ST3).

Moreover, the soft region specifying unit 24 specifies the soft region in the first and second primary ray images Gp1 and Gp2 (step ST4). Next, the indicator derivation unit 25 derives the first attenuation coefficient μ1 and the second attenuation coefficient μ2 according to the body thickness in the soft region for each of the first radiation image G1 and the second radiation image G2 (step ST5). Further, the indicator derivation unit 25 derives the attenuation ratio, which is the ratio between the first attenuation coefficient μ1 and the second attenuation coefficient 112 according to the body thickness, as the indicator C0 representing a quality of the radiation (step ST6).

Next, the subtraction unit 26 derives the composition image (step ST7), and the determination unit 27 determines whether or not the difference between the derived indicator C0 and the standard indicator Cb exceeds the predetermined threshold value Th1 (step ST8). In a case in which a positive determination is made in step ST8, the display controller 28 displays the composition image and the warning (step ST9), and the processing is terminated. In a case in which a negative determination is made in step ST7, the display controller 28 displays the composition image (step ST10), and the processing is terminated.

Here, the change in the quality of the radiation can be calibrated by measuring an aluminum semi-value layer. However, since the aluminum semi-value layer is a simple indicator of the quality of the radiation using aluminum as a material, the aluminum semi-value layer cannot be uniquely associated with the energy distribution of the radiation. For this reason, in the measurement of the quality of the radiation using the aluminum semi-value layer, the separation accuracy of the composition of the energy subtraction processing may not be sufficient. In addition, the work of measuring the aluminum semi-value layer imposes a heavy burden on the user.

In the present embodiment, the first attenuation coefficient μ1 and the second attenuation coefficient μ2 according to the body thickness in the soft region for each of the first radiation image G1 and the second radiation image G2 are derived, and the attenuation ratio R0(t) between the first attenuation coefficient μ1 and the second attenuation coefficient μ2 according to the body thickness t is derived as the indicator C0 representing the quality of the radiation. Therefore, it is possible to derive the indicator representing the quality of the radiation with higher accuracy than in a case of using the aluminum semi-value layer. In addition, it is possible to acquire the indicator C0 representing the quality of the radiation in the daily diagnosis work, such as the energy subtraction imaging, without performing the work of measuring the aluminum semi-value layer. Therefore, it is possible to know the change in the quality of the radiation without imposing the burden on the user.

In addition, by issuing the warning in a case in which the difference between the indicator C0 and the standard indicator Cb exceeds the predetermined threshold value Th1, it is possible to notify the user that the quality of the radiation is changed significantly. In this case, the user can perform the calibration work in order to compensate for the temporal change in the quality of the radiation based on the warning.

Note that, in the embodiment described above, the indicator C0 is derived by using the first and second primary ray images Gp1 and Gp2 from which the scattered ray components are removed from the first and second radiation images G1 and G2, but the present disclosure is not limited to this. The indicator C0 may be derived by using the first and second radiation images G1 and G2.

Also, in the embodiment described above, the first and second radiation images G1 and G2 are acquired by the one-shot method, but the present disclosure is not limited to this. The first and second radiation images G1 and G2 may be acquired by a so-called two-shot method in which the imaging is performed twice by using only one radiation detector. In a case of the two-shot method, a position of the subject H included in the first radiation image G1 and the second radiation image G2 may shift due to a body movement of the subject H. Therefore, in the first radiation image G1 and the second radiation image G2, it is preferable to perform the processing according to the present embodiment after registration of the subject is performed.

In addition, in the embodiment described above, the radiation image acquired in the system that images the subject H using the first and second radiation detectors 5 and 6 is used, but it is needless to say that the technology of the present disclosure can be applied even in a case in which the first and second radiation images G1 and G2 are acquired using an accumulative phosphor sheet instead of the radiation detector. In this case, the first and second radiation images G1 and G2 need only be acquired by stacking two accumulative phosphor sheets, emitting the radiation transmitted through the subject H, accumulating and recording radiation image information of the subject H in each of the accumulative phosphor sheets, and photoelectrically reading the radiation image information from each of the accumulative phosphor sheets. Note that the two-shot method may also be used in a case in which the first and second radiation images G1 and G2 are acquired by using the accumulative phosphor sheet.

In addition, the radiation in the embodiment described above is not particularly limited, and α-rays or γ-rays can be used in addition to X-rays.

In addition, in the embodiment described above, for example, various processors shown below can be used as the hardware structures of processing units that execute various pieces of processing, such as the image acquisition unit 21, the body thickness derivation unit 22, the scattered ray removal unit 23, the soft region specifying unit 24, the indicator derivation unit 25, the subtraction unit 26, the determination unit 27, and the display controller 28. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electrical circuit that is a processor having a circuit configuration which is designed for exclusive use in order to execute a specific processing, such as an application specific integrated circuit (ASIC).

One processing unit may be configured by one of these various processors, or may be configured by a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer of a client, a server, and the like there is an aspect in which one processor is configured by a combination of one or more CPUs and software and this processor functions as a plurality of processing units. Second, as represented by a system on chip (SoC) or the like, there is an aspect of using a processor that realizes the function of the entire system including the plurality of processing units by one integrated circuit (IC) chip. In this way, as the hardware structure, the various processing units are configured by using one or more of the various processors described above.

Further, as the hardware structures of these various processors, more specifically, it is possible to use an electrical circuit (circuitry) in which circuit elements, such as semiconductor elements, are combined.

The supplementary notes of the present disclosure will be described below.

Supplementary Note 1

A radiation image processing device comprising at least one processor, in which the processor acquires a first radiation image and a second radiation image, which are acquired by imaging a subject with radiation having different energy distributions, derives a body thickness of the subject based on at least one of the first radiation image or the second radiation image, specifies a soft region of the subject in the first radiation image and the second radiation image, derives a first attenuation coefficient and a second attenuation coefficient, which correspond to the body thickness in the soft region, for each of the first radiation image and the second radiation image, and derives an attenuation ratio, which is a ratio according to the body thickness between the first attenuation coefficient and the second attenuation coefficient, as an indicator representing a quality of the radiation.

Supplementary Note 2

The radiation image processing device according to Supplementary Note 1, in which the processor derives a first primary ray image and a second primary ray image by removing scattered ray components of the first radiation image and the second radiation image, and derives the first attenuation coefficient and the second attenuation coefficient based on the first primary ray image and the second primary ray image.

Supplementary Note 3

The radiation image processing device according to Supplementary Note 1 or 2, in which the indicator represents a relationship between the body thickness and the attenuation ratio.

Supplementary Note 4

The radiation image processing device according to any one of Supplementary Notes 1 to 3, in which the processor determines whether or not a difference between the indicator and a standard indicator exceeds a predetermined threshold value, and issues a warning in a case in which a negative determination is made in the determination.

Supplementary Note 5

A radiation image processing method comprising acquiring a first radiation image and a second radiation image, which are acquired by imaging a subject with radiation having different energy distributions, deriving a body thickness of the subject based on at least one of the first radiation image or the second radiation image, specifying a soft region of the subject in the first radiation image and the second radiation image, deriving a first attenuation coefficient and a second attenuation coefficient, which correspond to the body thickness in the soft region, for each of the first radiation image and the second radiation image, and deriving an attenuation ratio, which is a ratio according to the body thickness between the first attenuation coefficient and the second attenuation coefficient, as an indicator representing a quality of the radiation.

Supplementary Note 6

A radiation image processing program causing a computer to execute a procedure of acquiring a first radiation image and a second radiation image, which are acquired by imaging a subject with radiation having different energy distributions, a procedure of deriving a body thickness of the subject based on at least one of the first radiation image or the second radiation image, a procedure of specifying a soft region of the subject in the first radiation image and the second radiation image, a procedure of deriving a first attenuation coefficient and a second attenuation coefficient, which correspond to the body thickness in the soft region, for each of the first radiation image and the second radiation image, a procedure of deriving an attenuation ratio, which is a ratio according to the body thickness between the first attenuation coefficient and the second attenuation coefficient, as an indicator representing a quality of the radiation.

What is claimed is:

1. A radiography system comprising:
an imaging apparatus including:

a radiation source that emits radiation;

a first radiation detector that generates a first radiation image; and a second radiation detector that generates a second radiation image, the first radiation image and the second radiation image being acquired by imaging a subject with radiation having different energy distributions; and a radiation image processing device including at least one processor, wherein the processor acquires the first radiation image and the second radiation image, derives a body thickness of the subject based on at least one of the first radiation image or the second radiation image, specifies a soft region of the subject in the first radiation image and the second radiation image, derives a first attenuation coefficient and a second attenuation coefficient, which correspond to the body thickness in the soft region, for each of the first radiation image and the second radiation image, derives an indicator representing a quality of the radiation, the indicator being an attenuation ratio of the first attenuation coefficient to the second attenuation coefficient according to the body thickness, determines whether or not a difference between the indicator and a standard indicator exceeds a predetermined threshold value, and displays a warning on a display in a case in which a negative determination is made in the determination.

2. The radiography system according to claim 1, wherein the processor derives a first primary ray image and a second primary ray image by removing scattered ray components of the first radiation image and the second radiation image, and derives the first attenuation coefficient and the second attenuation coefficient based on the first primary ray image and the second primary ray image.

3. The radiography system according to claim 1, wherein the indicator represents a relationship between the body thickness and the attenuation ratio.

4. The radiography system according to claim 1, wherein the processor derives the first attenuation coefficient and the second attenuation coefficient based on pixel values of the soft region in a first primary ray image and a second primary ray image, the first primary ray image being obtained by removing a scattered ray component from the first radiation image, and the second primary ray image being obtained by removing the scattered ray component from the second radiation image.

5. The radiography system according to claim 2, wherein the indicator represents a relationship between the body thickness and the attenuation ratio.

6. A radiation image processing method for a radiography system comprising:

an imaging apparatus including:

a radiation source that emits radiation;

a first radiation detector that generates a first radiation image; and a second radiation detector that generates a second radiation image, the first radiation image and the second radiation image being acquired by imaging a subject with radiation having different energy distributions; and a radiation image processing device, the method comprising:

acquiring the first radiation image and the second radiation image;

deriving a body thickness of the subject based on at least one of the first radiation image or the second radiation image;

specifying a soft region of the subject in the first radiation image and the second radiation image;

deriving a first attenuation coefficient and a second attenuation coefficient, which correspond to the body thickness in the soft region, for each of the first radiation image and the second radiation image;

deriving an indicator representing a quality of the radiation, the indicator being an attenuation ratio of the first attenuation coefficient to the second attenuation coefficient according to the body thickness;

determining whether or not a difference between the indicator and a standard indicator exceeds a predetermined threshold value; and displaying a warning on a display in a case in which a negative determination is made in the determination.

7. A non-transitory computer-readable storage medium that stores a radiation image processing program for a radiography system comprising:

an imaging apparatus including:

a radiation source that emits radiation;

a first radiation detector that generates a first radiation image; and a second radiation detector that generates a second radiation image, the first radiation image and the second radiation image being acquired by imaging a subject with radiation having different energy distributions; and a radiation image processing device, the radiation image processing program causing a computer to execute:

a procedure of acquiring the first radiation image and the second radiation image;

a procedure of deriving a body thickness of the subject based on at least one of the first radiation image or the second radiation image;

a procedure of specifying a soft region of the subject in the first radiation image and the second radiation image;

a procedure of deriving a first attenuation coefficient and a second attenuation coefficient, which correspond to the body thickness in the soft region, for each of the first radiation image and the second radiation image;

a procedure of deriving an indicator representing a quality of the radiation, the indicator being an attenuation ratio of the first attenuation coefficient to the second attenuation coefficient according to the body thickness;

a procedure of determining whether or not a difference between the indicator and a standard indicator exceeds a predetermined threshold value; and a procedure of displaying a warning on a display in a case in which a negative determination is made in the determination.

* * * * *